(12) United States Patent
Siegler et al.

(10) Patent No.: US 7,745,121 B2
(45) Date of Patent: Jun. 29, 2010

(54) POLYMORPHISM IN THE MACROPHAGE MIGRATION INHIBITORY FACTOR (MIF) GENE AS MARKER FOR PROSTATE CANCER

(75) Inventors: Katherine Siegler, Seminole, FL (US); Kenneth Iczkowski, Gainesville, FL (US); Richard Bucala, Cos Cob, CT (US); Pedro L. Vera, Largo, FL (US)

(73) Assignee: The Department of Veterans Affairs, Washington, DC (US)

( * ) Notice: Subject to any disclaimer, the term of this patent is extended or adjusted under 35 U.S.C. 154(b) by 0 days.

(21) Appl. No.: 11/438,370

(22) Filed: May 23, 2006

(65) Prior Publication Data

US 2007/0048763 A1 Mar. 1, 2007

Related U.S. Application Data

(60) Provisional application No. 60/683,309, filed on May 23, 2005.

(51) Int. Cl.
*C12Q 1/68* (2006.01)
*C07H 21/04* (2006.01)
(52) U.S. Cl. .......................................... 435/6
(58) Field of Classification Search ................. 435/6
See application file for complete search history.

(56) References Cited

U.S. PATENT DOCUMENTS

| | | | |
|---|---|---|---|
| 6,287,772 B1 * | 9/2001 | Stefano et al. | 435/6 |
| 6,468,742 B2 * | 10/2002 | Nerenberg et al. | 435/6 |
| 6,821,727 B1 * | 11/2004 | Livak et al. | 435/6 |
| 6,902,900 B2 * | 6/2005 | Davies et al. | 435/6 |
| 6,905,829 B2 * | 6/2005 | Cho et al. | 435/6 |
| 7,205,107 B2 * | 4/2007 | Baugh et al. | 435/6 |
| 7,361,474 B2 * | 4/2008 | Siegler | 435/7.1 |
| 2001/0046670 A1 * | 11/2001 | Brookes | 435/6 |

FOREIGN PATENT DOCUMENTS

WO WO-00/20633 4/2000

OTHER PUBLICATIONS

Meyer-Siegler et al. (Cancer 94:1449-1456 (2002).*
Hutchinson's on-line dictionary definition for "chemiluminescence".*
Donn et al. Arthritis Rheum. 44:1782-1785 (2001).*
Donn et al. Arthritis Rheum. 46:2402-2409 (2002).*
Baugh et al. Genes & Immunity 3:170-176 (2002).*
Gerwirtz et al. (Blood 92(3): 712-736, 1998).*
Opalinska et al. (Nature Reviews 1:503-514, 2002).*
Ding et al. (J. Surgical Oncol. 100:106-110 (2009)).*
Li Gao et al. "Macrophage Migration Inhibitory Factor in Acute Lung Injury: Expression, Biomarker and Associations". Transl Res. 2007; 150(1): 18-29.
B. J. Plant et al. "Sarcoidosis and MIF gene polymorphism: a case-control study in an Irish population". Eur Respir J 2007; 29: 325-329.
Bianca Miterski et al. "Complex genetic predisposition in adult and juvenile rheumatoid arthritis". BMC Genetics 2004, 5:2, Feb. 4, 2004.
M. M. Amoli et al. "Lack of association between macrophage migration inhibitory factor gene (-173 G/C) polymorphism and cutaneous vasculitis". Clinical and Experimental Rheumatology 2006, pp. 576-579.
Timothy R. D. J. Radstake et al. "Correlation of Rheumatoid Arthritis Severity With the Genetic Functional Variants and Circulating Levels of Macrophage Inhibitory Factor". Arthritis & Rheumatism, vol. 52, No. 10, Oct. 2005, pp. 3020-3029.
Julia Dambacher et al. "Macrophage Migration Inhibitory Factor (MIF)—173G/C Promoter Polymorphism Influences Upper Gastrointestinal Tract Involvement and Disease Activity in Patients with Crohn's Disease." Inflamm Bowel Dis, vol. 13, No. 1, Jan. 2007, pp. 71-82.
Sou-Pan Wu et al. "Macrophage Migration . . . ". Arthritis and Rheumatism 54: 3661-3669, 2006.

* cited by examiner

*Primary Examiner*—Lynn Bristol
(74) *Attorney, Agent, or Firm*—Blank Rome LLP

(57) ABSTRACT

The present invention relates to the risk assessment, detection, diagnosis, or prognosis of prostate cancer. More specifically, this invention relates to the detection of certain polymorphism in the promoter region of the MIF gene to determine the risk, detect, diagnose, or prognosticate prostate cancer. Applicants have discovered that the presence of a −173C and/or −749 $(CATT)_{7\ or\ more}$ repeat predispose an individual to prostate cancer.

5 Claims, 4 Drawing Sheets

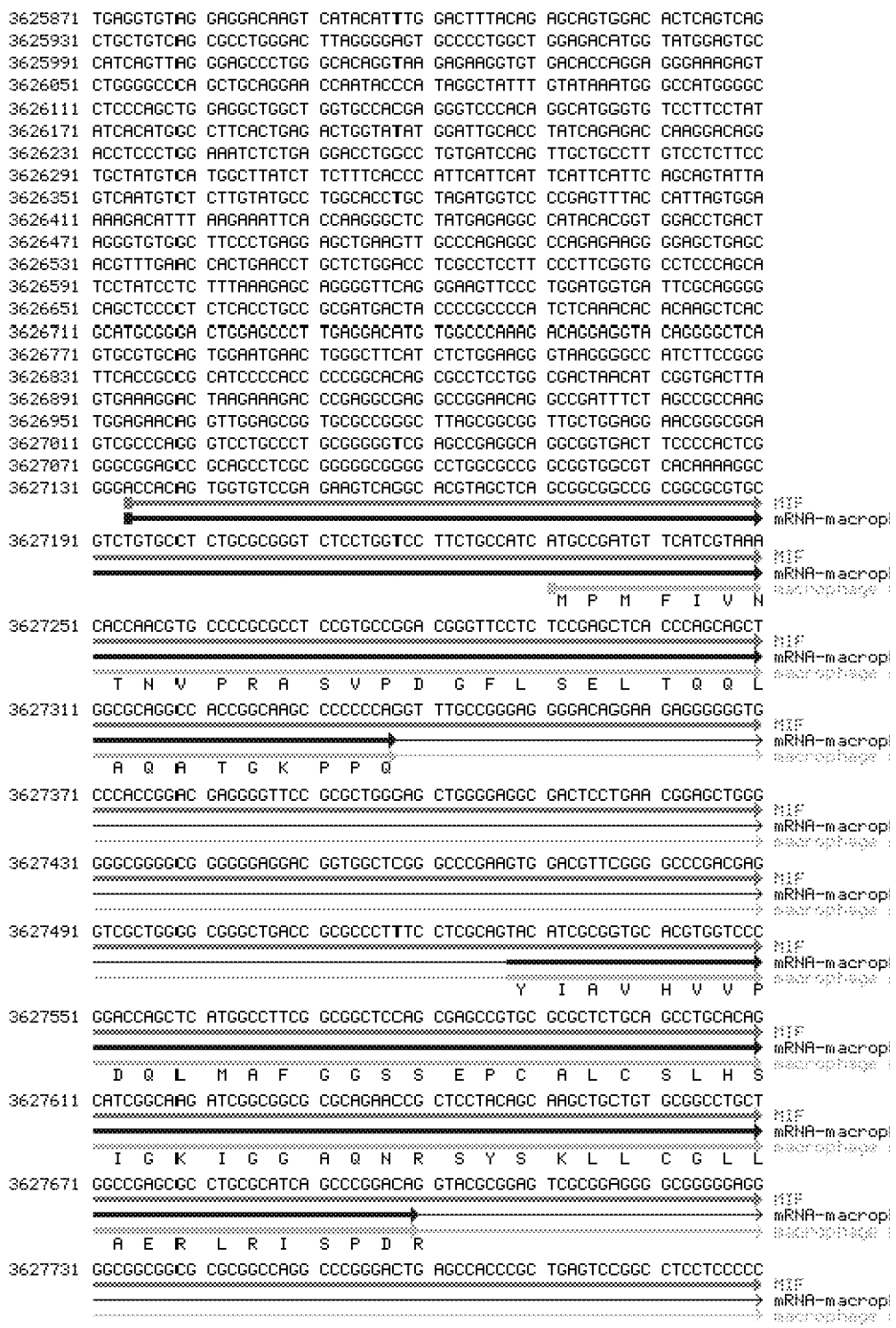
FIGURE 4 (SEQ ID NO: 1)

SEQUENCE LISTING

```
<160> NUMBER OF SEQ ID NOS: 1

<210> SEQ ID NO 1
<211> LENGTH: 1920
<212> TYPE: DNA
<213> ORGANISM: Homo sapiens

<400> SEQUENCE: 1
tgaggtgtag gaggacaagt catacatttg gactttacag agcagtggac actcagtcag      60
ctgctgtcag cgcctgggac ttaggggagt gcccctggct ggagacatgg tatggagtgc     120
catcagttag ggagccctgg gcacaggtaa gagaaggtgt gacaccagga gggaaagagt     180
ctggggccca gctgcaggaa ccaatacccca taggctattt gtataaatgg gccatggggc    240
ctcccagctg gaggctggct ggtgccacga gggtcccaca ggcatgggtg tccttcctat     300
atcacatggc cttcactgag actggtatat ggattgcacc tatcagagac caaggacagg     360
acctccctgg aaatctctga ggacctggcc tgtgatccag ttgctgcctt gtcctcttcc     420
tgctatgtca tggcttatct tctttcaccc attcattcat tcattcattc agcagtatta     480
gtcaatgtct cttgtatgcc tggcacctgc tagatggtcc ccgagtttac cattagtgga     540
aaagacattt aagaaattca ccaagggctc tatgagaggc catacacggt ggacctgact     600
agggtgtggc ttccctgagg agctgaagtt gcccagaggc ccagagaagg ggagctgagc     660
acgtttgaac cactgaacct gctctggacc tcgcctcctt cccttcggtg cctcccagca     720
tcctatcctc tttaaagagc aggggttcag ggaagttccc tggatggtga ttcgcagggg     780
cagctcccct ctcacctgcc gcgatgacta ccccgcccca tctcaaacac acaagctcac     840
gcatgcggga ctggagccct tgaggacatg tggcccaaag acaggaggta cagggctca     900 gtgcgtgcag tggaatgaac tgggcttcat ctctggaagg gtaagggcc atcttccggg     960 ttcaccgccg catccccacc cccggcacag cgcctcctgg cgactaacat cggtgactta    1020
gtgaaaggac taagaaagac ccgaggcgag gccggaacag gccgatttct agccgccaag    1080
tggagaacag gttggagcgg tgcgccgggc ttagcggcgg ttgctggagg aacgggcgga    1140
gtcgcccagg gtcctgccct gcggggggtcg agccgaggca ggcggtgact tccccactcg    1200
gggcggagcc gcagcctcgc gggggcgggg cctggcgccg gcggtggcgt cacaaaaggc    1260
gggaccacag tggtgtccga gaagtcaggc acgtagctca gcggcggccg cggcgcgtgc    1320
gtctgtgcct ctgcgcgggt ctcctggtcc ttctgccatc atgccgatgt tcatcgtaaa    1380
caccaacgtg ccccgcgcct ccgtgccgga cgggttcctc tccgagctca cccagcagct    1440
ggcgcaggcc accggcaagc ccccccaggt ttgccgggag gggacaggaa gagggggtg    1500 cccaccggac gaggggttcc gcgctgggag ctggggaggc gactcctgaa cggagctggg    1560
gggcggggcg gggggaggac ggtggctcgg gcccgaagtg gacgttcggg gcccgacgag    1620
gtcgctgggg cgggctgacc gcgcccttc ctcgcagtac atcgcggtgc acgtggtccc    1680
ggaccagctc atggccttcg gcggctccag cgagccgtgc gcgctctgca gcctgcacag    1740
```

```
                                    -continued
catcggcaag atcggcggcg cgcagaaccg ctcctacagc aagctgctgt gcggcctgct    1800
ggccgagcgc ctgcgcatca gcccggacag gtacgcggag tcgcggaggg gcggggagg     1860 ggcggcggcg cgcggccagg cccgggactg agccacccgc tgagtccggc ctcctccccc    1920
```

POLYMORPHISM IN THE MACROPHAGE MIGRATION INHIBITORY FACTOR (MIF) GENE AS MARKER FOR PROSTATE CANCER

This application claims priority to U.S. Provisional Patent Application No. 60/683,309, filed May 23, 2005, which is incorporated herein by reference.

FIELD OF THE INVENTION

The present invention relates to the risk assessment, detection, diagnosis, or prognosis of prostate cancer (CaP). More specifically, this invention relates to the detection of certain polymorphism in the promoter region of the MIF gene to determine the risk, detect, diagnose, or prognosticate prostate cancer.

BACKGROUND OF THE INVENTION

Prostate cancer is the most common form of cancer among males. Overwhelming clinical evidence shows that human prostate cancer has the propensity to metastasize to bone, and the disease appears to progress inevitably from androgen dependent to androgen refractory status, leading to increased patient mortality. This prevalent disease is currently the second leading cause of cancer death among men in the U.S.

In spite of considerable research into therapies for the disease, prostate cancer remains difficult to treat. Commonly, treatment is based on surgery and/or radiation therapy, but these methods are ineffective in a significant percentage of cases. Two previously identified prostate specific proteins—prostate specific antigen (PSA) and prostatic acid phosphatase (PAP)—have limited therapeutic and diagnostic potential. For example, serum PSA concentrations do not always correlate well with the presence of prostate cancer, being positive in a percentage of non-prostate cancer cases, and serum PSA concentrations do not correlate with cancer severity.

Current clinical practice includes routine prostate cancer screening in men over the age of forty for prostate cancer. This screening involves looking for the protein prostate specific antigen (PSA) in the blood. This test does not always identify patients with prostate cancer and can't identify aggressive prostate cancer. Patients exhibit extreme variation in the progression of their prostate cancer. In some the cancer remains confined to the prostate and causes no harm to the patient. In others, the cancer spreads quickly throughout the body, especially to the bones. There are no accurate methods to determine the aggressiveness of prostate cancer. Therefore, the physician treating this disease does not have reliable ways to determine whether the prostate cancer will spread. The current treatments for prostate cancer often have significant negative effects on patient quality of life. This situation makes it difficult for the physician to make proper treatment decisions.

Using the technique of differential display polymerase chain reaction, it was found that the cytokine, macrophage migration inhibitory factor (MIF), is one gene whose expression is altered in metastatic prostate cancer when compared to normal tissue (Meyer-Siegler et al. (1996), *Urology* 48: 448-452).

MIF was first described thirty years ago and was designated as a cytokine, a chemical mediator, which regulates cell growth by inducing the expression of specific target genes. The initial described function of MIF was as a regulator of inflammation and immunity. It is expressed in the brain, and eye lens, is a delayed early response gene in fibroblasts, and it has been reported that this protein can be found in prostate tissues. MIF has been shown to be a pituitary, as well as macrophage cytokine and a critical mediator of septic shock. Recent studies also suggest that MIF may have an autocrine function for embryo development and is produced by the Leydig cells of the testes. Thus, it appears that this cytokine may play a fundamental role in cell growth regulation and possibly development.

U.S. Pat. No. 6,043,044 discloses the use of prostate tissue extracts as a patient sample to determine the amount of MIF. Immuno- and RNA blot analysis performed using homogenized tissue that contains variable proportions of epithelial and stromal cells still determined significant differences in the levels of MIF protein produced by metastatic tissue (490.3+/−71.3 ng/mg total protein). In practice this test was unreliable and difficult to perform because of contamination with surrounding connective and stromal tissue. It does not have utility in patient diagnosis or prognosis. Further, the patent does not mention or correlate serum MIF levels with prostate cancer.

There are currently very few genetic methods available for the diagnosis and prevention of prostate cancer. Thus, the identification of genetic polymorphisms controlling MIF expression, that are responsible for predisposition of prostate cancer would provide for a better understanding of the mechanisms of cancer causation (including ethnic and individual susceptibility), and ultimately lead to ways of prostate cancer prevention. The present invention addresses these disadvantages present in the prior art and provides an improved assay with commercial application that is less invasive than that of the prior art.

SUMMARY OF THE INVENTION

Two functional promoter polymorphisms of the MIF gene were previously described. Donn et al. (A novel 5'-flanking region polymorphism of macrophage migration inhibitory factor is associated with systemic-onset juvenile idiopathic arthritis. *Arthritis Rheum* 2001; 44:1782-5) identified a single nucleotide polymorphism (SNP) in the 5' region at −173 nucleotides. It has been demonstrated that the mutant allele −173 C (where the G at position −173 in the normal MIF gene is replaced with C) is associated with increased MIF protein production (Donn et al. Mutation screening of the macrophage migration inhibitory factor gene: positive association of a functional polymorphism of macrophage migration inhibitory factor with juvenile idiopathic arthritis. *Arthritis Rheum* 2002; 46:2402-9). Tetranucleotide CATT repeat, starting at position −749, is an additional MIF gene polymorphism upstream of the −173 position that is associated with MIF protein amounts and rheumatoid arthritis disease severity (Baugh et al. A functional promoter polymorphism in the macrophage migration inhibitory factor (MIF) gene associated with disease severity in rheumatoid arthritis. *Genes Immun* 2002; 3:170-6). A $(CATT)_5$ repeat is associated with reduced MIF amounts and less severe rheumatoid arthritis.

In addition, the present inventors have discovered that the −173 C and/or the −749 CATT tetranucleotide repeat is associated with susceptibility and severity of prostate cancer. Therefore, the present invention relates to polymorphisms in the MIF genes, particularly in the promoter region, more particularly to the −173 C and/or the CATT repeat; and to methods of using such mutations in the diagnosis and treatment of inheritable prostate cancer susceptibility.

One aspect of the invention relates to the identification of the polymorphisms by hybridization, polymorphism and/or sequence analysis. Preferably, DNA is isolated from peripheral (blood) lymphocytes and analyzed for specific mutations by SSCP (single-strand conformation dependent DNA polymorphism) scanning and direct PCR (polymerase chain reaction) sequencing. The inheritance pattern of the specified gene polymorphisms are used to diagnose genetic susceptibility in men who are genetically at increased risk for developing prostate cancer or has already developed prostate cancer.

Other aspects of the invention include genetic probes comprising sequences complementary to the sequences containing the specified polymorphisms; cloning or expression vectors containing the nucleic acid sequences; host cells or organisms transformed with these expression vectors; methods for production and recovery of purified polypeptides from host cells; and the purified polypeptides themselves. Preferred embodiments include labeled binding agents, including antibodies, specific for the polypeptides encoded by the disclosed nucleic acids, which can be used to identify expression products of these diagnostic polymorphisms or alleles in patient derived fluid or tissue samples.

Yet other aspects of the invention relate to methods of using these nucleotide sequences or their complements, or fragments thereof, as hybridization probes, as oligomers for PCR, for chromosome and gene mapping, in the recombinant production of protein, and in generation of anti-sense DNA or RNA, their chemical analogs and the like.

For therapeutic intervention, the invention provides compositions which can functionally interfere with the transcription or translation products of the mutations and/or alleles within the specified MIF genes associated with prostate cancer susceptibility. These include antisense nucleic acids, competitive peptides, encoded by the disclosed nucleic acids, and high affinity binding agents such as antibodies.

The diagnostic methods of the present invention can be used alone or in conjunction with the commonly used PSA test or other available diagnostic tests for prostate cancer. When used in conjunction with the PSA test, patients most at risk for prostate cancer would have elevated levels of both PSA and the presence of the −173 C and/or the CATT repeat polymorphism. Another test may include the androgen-metabolic gene mutation disclosed in U.S. Pat. No. 6,395,479, which is incorporated herein by reference.

BRIEF DESCRIPTION OF THE DRAWINGS

FIG. 4 shows the genomic MIF gene.

DETAILED DESCRIPTION OF THE PREFERRED EMBODIMENT

Figure 1:
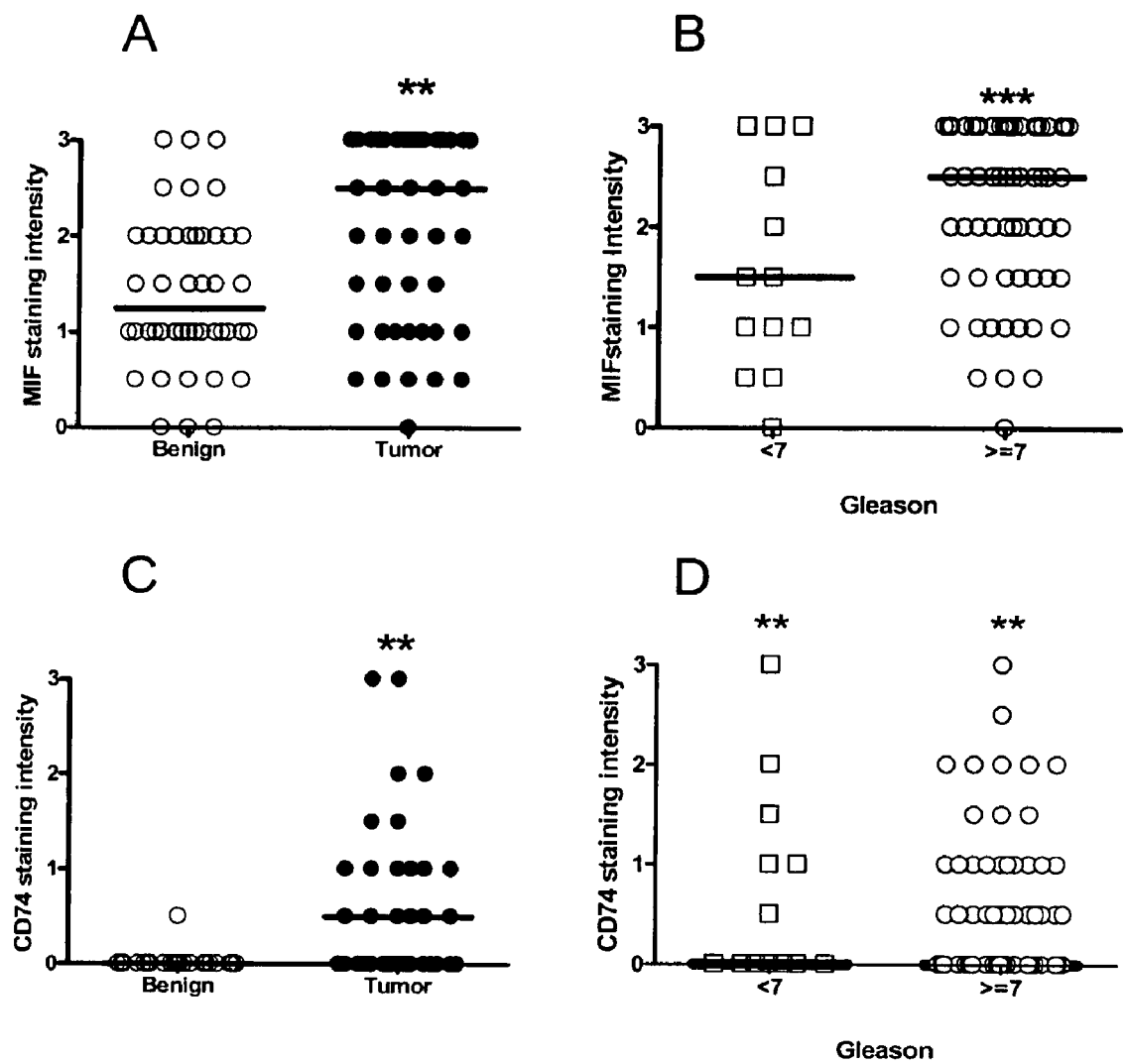
FIG. 1 is a plot showing the immunostaining intensity of MIF and CD74 in benign and cancerous regions of the prostate.

As described herein, the present invention provides a number of nucleotide sequences comprising mutations and/or alleles within the MIF gene, and methods of use in the diagnosis and treatment of prostate cancer susceptibility. The disclosed mutations within the gene include a substitution at the −173 position (173 nucleic acids upstream of the start codon) where the G is replaced with a C (herein referred to as −173C), and a CATT repeat upstream of −173 position. The −173C mutation may occur in one or in both alleles of the MIF gene; however, a single occurrence is sufficient to increase the prostate cancer risk of an individual. Likewise, the presence of CATT repeat, preferably 7 or higher repeat (located 794 nucleotides upstream from the start codon), significantly increase the prostate cancer risk of an individual. Genomically, the MIF gene is located is on chromosome 22q11.23, the sequence of which is given in SEQ ID NO:1 and FIG. 4. In FIG. 4, the CATT repeat starts at 3626320 and the −173 repeat is located at 3626964. FIG. 4 depicts $(CATT)_5$ and −173G, which are the wild genotypes. The sequences falling within the scope of the present invention are not limited to the specific sequences herein described, but also include nucleic acid sequences coding for the same amino acid sequences as do the disclosed sequences to accommodate for codon variability. The present inventors have discovered that the presence of these polymorphisms indicates an increased risk of prostate cancer. To that end, detection of the −173C and/or the CATT repeat in the promoter region of the MIF gene are useful in determining the risk of, detecting, diagnosing, or prognosticating prostate cancer.

Also included within the scope of the specified nucleic acid sequences of the invention are antisense polynucleotides, i.e. nucleic acid sequences that hybridize under stringent conditions to a fragment of the DNA sequences carrying the specified polymorphisms, which fragment is greater than about 10 bp, preferably 20-50 bp, and even greater than 100 bp. These antisense polynucleotides are useful as probes for detecting the polymorphisms or as therapeutic agents in antisense therapy for the treatment of prostate cancer.

Methods of Detection

The present invention provides a method of identifying nucleic acid sequences containing the specified polymorphism. The method generally comprises detecting the polymorphism in a nucleic acid sample from an individual. In detail, this method comprises (i) amplifying a DNA fragment comprising an individual's protein-coding sequence of the MIF gene, (ii) comparing this DNA fragment to the sequence of the wildtype gene, and (iii) determining the presence or absence of polymorphisms in this DNA fragment. Nucleic acid samples used in the methods and assays of the present invention may be prepared by any available method or process.

Detection of point mutations may be accomplished by molecular cloning of the specified allele and subsequent sequencing of that allele using techniques well known in the art. Alternatively, the gene sequences may be amplified directly from a genomic DNA preparation from the tumor tissue using PCR, and the sequence composition is determined from the amplified product.

The PCR reaction is well known in the art (See, e.g., U.S. Pat. Nos. 4,683,203; and 4,683,195). In general, the PCR procedure describes a method of gene amplification which is comprised of (i) sequence-specific hybridization of primers to specific genes within a DNA sample (or library), (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization, i.e. each primer is specifically designed to be complementary to each strand of the genomic locus to be amplified. The primers are prepared using any suitable method, such as conventional phosphotriester or phosphodiester methods or automated embodiments thereof (Beaucage, Tet. Lett. 22:1859-1862, 1981).

The polymerization agent can be any compound or system (including enzymes) which will facilitate combination of the nucleotides in the proper manner to form the primer extension products which are complementary to each nucleic acid strand. Other fundamental conditions to allow amplification include the presence of nucleoside triphosphates and suitable temperature and pH (Thigpen et al., *J. Clin. Invest.* 90: 799-809, 1992; Saiki et al., *Science* 239: 487-491, 1988).

The presence of a susceptibility allele can be established using well-known methods, some of them based on differences in hybridization of mutated against wild-type DNA segments. These methods include, but are not limited to, single-strand conformation polymorphism (SSCP) (Thigpen et al., 1992; Orita et al., *PNAS USA* 86: 2766-2770, 1989), denaturing gradient gel electrophoresis (DGGE) (Finke, *Exp. Clin. Endocrinol. Diabetes* 104 (suppl): 92-97, 1996; Wartell et al., *Nucl. Acids Res.* 18:2699-1705, 1990; Sheffield et al., *PNAS USA* 86:232-236, 1989), RNase protection assays (Peltonen et al., *Ann. Clin. Res.* 18:224-230, 1986; Osborne et al., *Cancer Res.* 51:6194-6198, 1991), allele-specific oligonucleotides (Wu et al., *DNA* 8:135-142, 1989), allele-specific PCR (Finke, 1996), and the use of proteins which recognize nucleotide mismatches, such as the *E. coli* mutS protein (Han et al., *Nuc. Acids Res. Supp.* 2(1):287-288, 2002). In addition, restriction fragment length polymorphism (RFLP) probes for the gene or surrounding marker genes can be used to score alteration of an allele or an insertion in a polymorphic fragment.

In the first three methods, the appearance of a new electrophoretic band is observed by polyacrylamide gel electrophoresis. SSCP detects the differences in speed of migration of single-stranded DNA sequences in polyacrylamide gel electrophoresis under different conditions such as changes in pH, temperature, etc. A variation in the nucleotide base sequence of single-stranded DNA segments (due to mutation or polymorphism) may lead to a difference in spatial arrangement and thus in mobility. DGGE exploits differences in the stability of DNA segments in the presence or absence of a mutation. Introduction of a mutation into double-stranded sequences creates a mismatch at the mutated site that destabilizes the DNA duplex. Using a gel with an increasing gradient of formamide (denaturation gradient gel), the mutant and wild-type DNA can be differentiated by their altered migration distances. The basis for the RNase protection assay is that the RNase A enzyme cleaves mRNA that is not fully hybridized with its complementary strand, whereas completely hybridized duplex is protected from RNase A digestion. The presence of a mismatch results in incomplete hybridization and thus cleavage by RNase A at the mutation site. Formation of these smaller fragments upon cleavage can be detected by polyacrylamide gel electrophoresis. Techniques based on mismatch detection are generally being used to detect point mutations in a gene or its mRNA product. While these techniques are less sensitive than sequencing, they are simpler to perform on a large number of tumor samples. In addition to the RNase A protection assay, there are other DNA probes that can be used to detect mismatches, through enzymatic or chemical cleavage. See, e.g., Smooker et al., *Mutat. Res.* 288:65-77, 1993; Cotton et al., *PNAS USA* 85:4397, 1988; Shenk et al., *PNAS USA* 72:989, 1975). Alternatively, mismatches can also be detected by shifts in the electrophoretic mobility of mismatched duplexes relative to matched duplexes (Cariello, *Human Genetics* 42:726, 1988). With either riboprobes or DNA probes, the cellular mRNA or DNA which may contain a mutation can be amplified using PCR prior to hybridization. Changes in DNA of the gene itself can also be detected using Southern hybridization, especially if the changes are gross rearrangements, such as deletions and insertions.

DNA sequences of the specified gene which have been amplified by use of polymerase chain reaction may also be screened using allele-specific oligonucleotide probes. These probes are nucleic acid oligomers, each of which is complementary to a corresponding segment of the investigated gene and may or may not contain a known mutation. The assay is performed by detecting the presence or absence of a hybridization signal for the specific sequence. In case of allele-specific PCR, the PCR technique uses unique primers which selectively hybridize at their 3' ends to a particular mutated sequence. If the particular mutation is not present, no amplification product is observed.

Oligonucleotide Probes

Another aspect of the subject invention is to provide for polypeptide-specific nucleic acid hybridization probes capable of detecting polynucleotide polymorphisms associated with the MIF gene which predispose an individual to prostate cancer. The hybridization probes of the subject invention may be derived from the disclosed nucleotide sequences carrying the polymorphisms and form stable hybrids with the target sequences, under stringent to moderately stringent hybridization and wash conditions. Stringent conditions will be used in the case of perfect complimentarity with the target sequence, less stringent hybridization conditions will be used if mismatches are expected among the variants. Conditions will always be chosen such that nonspecific/adventitious bindings are eliminated or minimized. The probes may be of any suitable length, which span all or a portion of the specified gene region, and which allow specific hybridization.

Nucleic acid hybridization simply involves contacting a probe and target nucleic acid (from a nucleic acid sample) under conditions where the probe and its complementary target can form stable hybrid duplexes through complementary base pairing (see U.S. Pat. No. 6,333,155). Methods of nucleic acid hybridization are well known in the art. In a preferred embodiment, the probes are immobilized on solid supports such as beads, microarrays, or gene chips.

The probes include an isolated polynucleotide, preferably attached to a label or reporter molecule, may be used to isolate other polynucleotide sequences, having sequence similarity by standard methods. Techniques for preparing and labeling probes are known in the art and disclosed in Sambrook et al. (Molecular Cloning: A Laboratory Manual, Ed. 2; Cold Spring Harbor, N.Y.: Cold Spring Harbor Laboratory, 1989) or Ausubel et al. (Current Protocols in Molecular Biology, Wiley & Sons, New York, N.Y, 1995). The labels may be incorporated by any of a number of means well known to those of skill in the art (see U.S. Pat. No. 6,333,155). Commonly employed labels include, but are not limited to, biotin, fluorescent molecules, radioactive molecules, chromogenic substrates, chemiluminescent labels, enzymes, and the like. The methods for biotinylating nucleic acids are well known in the art, as are methods for introducing fluorescent molecules and radioactive molecules into oligonucleotides and nucleotides.

Other similar polynucleotides may be selected by using homologous polynucleotides. Alternatively, polynucleotides encoding these or similar polypeptides may be synthesized or selected by use of the redundancy in the genetic code. Various codon substitutions may be introduced, e.g., by silent changes (thereby producing various restriction sites) or to optimize expression for a particular system. Mutations may be introduced to modify the properties of the polypeptide, perhaps to change ligand-binding affinities, interchain affinities, or the polypeptide degradation or turnover rate.

Probes comprising synthetic oligonucleotides or other polynucleotides of the present invention may be derived from naturally occurring or recombinant single- or double-stranded polynucleotides, or be chemically synthesized. Probes may also be labeled by nick translation, Klenow fill-in reaction, or other methods known in the art.

Other means for producing specific hybridization probes for nucleic acids include the cloning of nucleic acid sequences into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

The nucleotide sequences may be used to construct hybridization probes for mapping their respective genomic sequences. The nucleotide sequence provided herein may be mapped to a chromosome or specific regions of a chromosome using well known genetic and/or chromosomal mapping techniques. These techniques include in situ hybridization, linkage analysis against known chromosomal markers, hybridization screening with libraries or flow-sorted chromosomal preparations specific to known chromosomes, and the like (Verma et al., Human Chromosomes: A Manual of Basic Techniques, Pergamon Press, New York N.Y, 1988).

To detect the presence of the mutations and/or alleles within the MIF gene predisposing an individual to prostate cancer, a test sample is prepared and analyzed for the presence or absence of such susceptibility alleles. Thus, the present invention provides methods to identify the expression of one of the nucleic acids of the present invention, or homolog thereof, in a test sample, using a nucleic acid probe or antibodies of the present invention. In particular, such methods comprise incubating a test sample with one or more of oligonucleotide probes of the present invention (as described above) and assaying for binding of the nucleic acid probes or antibodies to components within the test sample.

Conditions for incubating a nucleic acid probe or antibody with a test sample depend on the format employed in the assay, the detection methods used, and the type and nature of the probe used in the assay. One skilled in the art will recognize that any one of the commonly available hybridization or amplification formats can readily be adapted to employ the nucleic acid probes or antibodies of the present invention. Examples of such assays can be found in Chard, An Introduction to Radioimmunoassay and Related Techniques, Elsevier Science Publishers, Amsterdam, Netherlands, 1986; Bullock et al., Techniques in Immunocytochemistry, Academic Press, Orlando, Fla. Vol. 1, 1982, Vol. 2, 1983, Vol. 3, 1985; Tijssen, Practice and Theory of Immunoassays: Laboratory Techniques in Biochemistry and Molecular Biology, Elsevier Science Publishers, Amsterdam, Netherlands, 1985.

The test samples of the present invention include cells, protein or membrane extracts of cells, or biological fluids such as sputum, blood, serum, plasma, or urine. The test sample used in the above-described method will vary based on the assay format, nature of the detection method and the tissues, cells or extracts used as the sample to be assayed. Methods for preparing DNA extracts from any of the above samples are well known in the art and can be readily be adapted in order to obtain a sample which is compatible with the system utilized.

Drug Screening Assay

In addition, the defective nucleic acid sequences can provide a target for therapeutic intervention. Binding agents that are specific for the defective MIF gene and can be used for chemopreventive intervention. Accordingly, the present invention further provides methods of obtaining and identifying agents which bind to one of the defective nucleic acid sequences.

Preferably, the method comprises (i) contacting an agent with a nucleic acid sequence containing the −173C or the CATT repeat of the present invention; and (ii) determining whether the agent binds to this particular protein or nucleic acid. The binding activity of the agent is measured to determine if the agent is capable of modulating the MIF gene.

The agents screened in the above assay can be, but are not limited to, peptides, small molecules, vitamin derivatives, carbohydrates, and nucleic acids, or other pharmaceutical agents. Such binding agents are obtained in various ways, including random selection and screening of existing, large libraries of natural and synthetic molecules or rational design using protein modeling techniques.

For random screening, agents, such as peptides, carbohydrates, pharmaceutical agents, or the like, are selected at random and are assayed for their ability to bind to the protein encoded by a specified nucleic acid sequence of the present invention. Alternatively, agents may be rationally selected or designed. As used herein, an agent is said to be "rationally selected or designed" when the agent is chosen based on the configuration of the particular protein. For example, one skilled in the art can readily adapt currently available procedures to generate peptides, pharmaceutical agents and the like capable of binding to a specific peptide sequence in order to generate rationally designed antisense peptides, pharmaceutical agents, or the like. See, e.g., Hurby, Application of Synthetic Peptides: Antisense Peptides, In Synthetic Peptides, A User's Guide, W. H. Freeman, NY, pp. 289-307, 1992; and Kaspczak, *Biochemistry* 28:9230-8, 1989, Gene Therapy According to the present invention, a method is also provided of supplying wild-type function to a cell which carries mutant alleles. The wild-type MIF gene or a part thereof (especially the promoter region that carries the wild-type −173G or the CATT repeat) may be introduced into the cell in a vector such that the gene remains extrachromosomal or may be chromosomally incorporated. In such a situation, the MIF gene expression will be controlled by the inserted wild-type gene or portion thereof. More preferred is the situation where the wildtype gene or a part thereof is introduced into the mutant cell in such a way that it recombines with the endogenous mutant gene present in the cell. Such recombination requires a double recombination event which results in the correction of the gene mutation. Vectors for introduction of genes both for recombination and for extrachromosomal maintenance are known in the art, and any suitable vector may be used. Methods for introducing DNA into cells such as electroporation, calcium phosphate coprecipitation and viral transduction are known in the art, and the choice of method is within the competence of one skilled in the art.

As generally discussed above, the specified MIF genes or a fragment thereof, where applicable, may be employed in gene therapy methods in order to alter the amount of the expression products of such genes in cancer cells. Such gene therapy is particularly appropriate for use in both cancerous and pre-cancerous cells, in which the level of the encoded polypeptide differs compared to normal or in those tumor cells in which the mutant gene is expressed at a "normal" level, but the gene product is affected in its performance. Gene therapy would be carried out according to generally accepted methods, for example, as described in Therapy for Genetic Disease, T. Friedman, ed., Oxford University Press, pp. 105-121.

Without further description, it is believed that one of ordinary skill in the art can, using the preceding description and the following illustrative examples, make and utilize the compounds of the present invention and practice the claimed methods. The following example is given to illustrate the present invention. It should be understood that the invention is not to be limited to the specific conditions or details described in this example.

EXAMPLE

The aims of these studies were to examine the role of the MIF-173 G/C SNP and/or the CATT tetranucleotide repeat in predicting prostate cancer, serum MIF amounts, prostate tumor Gleason sum, and prostate cancer recurrence. The described patient samples (73 normal and 77 prostate cancer) were from the patients undergoing routine PSA screening at the Bay Pines VAMC and from patient prostate tissue samples from the Malcolm Randall VAMC.

Methods

Immunohistochemistry

Prostate tissue arrays from low Gleason sum tumors (Ambion) and high Gleason sum tumors (Imgenex), as well as archived prostate cancer tissue samples from radical prostatectomy (n=18) were processed for antigen retrieval using citrate buffer, pH 6.0 as described previously (Meyer-Siegler et al., *BMC Cancer* 5:73, 2005). Endogenous peroxidase was quenched with 2 min exposure to 3% hydrogen peroxide followed by blocking with 3% normal donkey serum for 30 min. Tissue was exposed to either anti-MIF biotinylated polyclonal antibody (BAF289, R&D Systems, 1:1000 in PBS, 0.3% Triton X-100) or anti-CD74 polyclonal antibody (sc-5438, Santa Cruz, 1:400 in PBS, 0.3% Triton X-100) overnight at 4 C. Tissue was then processed as described previously (Meyer-Siegler et al., *BMC Cancer* 5:73, 2005). Tissue staining in tumor and benign regions of the same sample was then scored for location and intensity (0=no staining detected through 3=very strong staining). Differences in epithelial staining intensity in matched benign versus tumor regions were assessed using paired, two-tailed t-tests. Data are expressed as median±interquartile range.

Study Subjects and Specimens

Approval for this study was obtained from the Bay Pines VA Healthcare System Institutional Review Board. The serum samples were obtained with waiver of informed consent under section 46.16(d) of the Department of Health and Human Services human subject regulation at 45 CFR 46. This study was a retrospective analysis of patients undergoing routine PSA screening at the Bay Pines VA Healthcare System and from archived patient prostate tissue samples from the Malcolm Randall VA Medical Center. Random serum samples remaining following routine PSA evaluation were collected the day that they were drawn and stored at −80 C. Patient age, ethnicity and clinical PSA values were obtained through analysis of computerized records.

Inclusion criteria for the prostate cancer cohort were documented diagnosis of prostate cancer with an available Gleason sum evaluation, as well as age at the time the sample was obtained. Serum samples for MIF analysis were available from 74 prostate cancer patients and archived prostate tissue remaining following radical prostatectomy were available from 18 prostate cancer patients. Patients with prostate cancer were enrolled regardless of treatment. Five year follow-up PSA amounts were available for 42 prostate cancer patients. Inclusion criteria for the control cohort were absence of documented diagnosis of cancer and/or chronic inflammatory disease and age at the time the sample was obtained. Controls were enrolled regardless of the serum PSA amounts. Serum samples for MIF analysis were available from 39 controls.

DNA Extraction and Genotyping

Genomic DNA was isolated from serum or prostate tissues using DNAzol (Invitrogen) followed by overnight strand displacement amplification (GenomiPhi, GE Healthcare). DNA quality was assessed by electrophoresis on 0.8% agarose gels (Invitrogen).

Serum MIF

Serum MIF was determined using a human MIF ELISA kit (R&D Systems, DuoSet ELISA) with the modifications described previously (Meyer-Siegler et al., *BMC Cancer* 5:73, 2005).

Statistical Analyses

Differences in population characteristics (age, serum MIF and PSA at time sample was obtained) and were analyzed using Student's t-test or Mann-Whitney U test, where appropriate. Differences in allele frequencies were analyzed by Chi-squared. Backwards stepwise logistic regression was used to assess the effect of Mif polymorphisms on prostate cancer risk and to assess whether these polymorphisms were associated with increased Gleason sum. Cox proportional hazards analysis was used to determine the association of prostate cancer recurrence as measured by biochemical failure (defined as two PSA values of 0.4 ng/ml or greater and rising or initiation of adjuvant therapy five years post prostate cancer-diagnosis) with Mif polymorphisms. The prostate cancer patients were on average 8 years older than the benign controls, therefore all odds ratio estimates of relative risk were adjusted for age as a continuous covariant in the regression analysis. Haplotype frequencies were determined using PHASE v2.1.1, Chi-squared was analyzed using GraphPad Prism version 4.00 (GraphPad Software, San Diego, Calif.), all other analyzes were performed using SPSS v14. P values less than or equal to 0.05 were considered statistically significant in all analyses.

Results

MIF and CD 74 Protein Expression in Human Prostate

MIF amounts were significantly increased in the serum of prostate cancer patients with a strong association with increasing Gleason sum (Muramaki et al., *Oncol Rep* 15: 253-257, 2006). However, the association of tissue MIF expression and the expression of the MIF receptor, CD74 in high Gleason sum tumors has not been well documented. MIF immunostaining was evident in both cancerous and benign regions of the prostate (n=46). MIF protein was localized predominately within the epithelium with the median staining score in the tumor regions (2.5±2.0) significantly higher than in benign regions (1.25±1.0) (FIG. 1 A). CD74 staining was localized within the epithelium of the tumor regions (0.5±1.0) with little or no immunostaining evident in the benign regions of the prostate (median score 0.0, range 0.0 to 0.5) (FIG. 1C).

MIF and CD74 staining scores in tumor regions were then compared to Gleason sum using a cutoff of Gleason sum less than 7 versus Gleason sum 7 or greater (FIGS. 1B and 1D). Staining intensity within the Gleason categories was compared to the theoretical median determined for the benign prostate regions by Wilcoxon Signed Rank test. Gleason sum 7 or greater prostate tumors exhibit greater MIF immunostaining (p<0.0001) compared to the theoretical median (1.25), which was not evident in the Gleason sum less than 7 tumors (p=0.19). Similar results were observed for CD74 immunostaining with Gleason sum less than tumors as well as Gleason sum 7 or greater tumors exhibiting increased immunostaining when compared to the theoretical median (0.0, p<0.01).

Study Population

The ethnic background for the entire cohort was 95.3% Caucasian, 2.7% African American and 2% other. The median age of the prostate cancer cohort (72, range 43-87 years) was higher (p<0.0001, Mann Whitney) than the controls (64, range 36-87 years). There was no difference in the serum PSA at the time of sampling between the prostate cancer and control groups (p=0.16). However, as we have documented previously, median serum MIF amounts in the prostate cancer cohort (7.7 ng/ml, range 1.3-28.3 ng/ml) were higher (p<0.0001, Mann Whitney) compared to controls (2.8 ng/ml, range 0.2-9.6 ng/ml).

Mif Polymorphism Allele and Haplotype Frequencies

The allelic distributions in either the prostate cancer or the benign controls for the Mif −173C polymorphism (P=0.9672 and P=0.3768, respectively) and the −794 Mif $(CATT)_{5-8}$ polymorphism (P=0.8358 and P=0.6066, respectively) were in accordance with the Hardy-Weinberg equilibrium.

Allelic and estimated haplotype frequencies for both polymorphisms in the prostate cancer and benign groups are listed in Table 1:

TABLE 1

Allele frequencies for the Mif-173 C and Mif $(CATT)_{5-8}$ polymorphisms and estimated haplotype frequencies in patients with prostate cancer (cases) and benign prostate (controls).

|  | Cases % | Controls % | p Value |
|---|---|---|---|
| Mif-173 C genotype |  |  |  |
| Allele frequency |  |  | <0.001 |
| G | 35.7 | 79.5 |  |
| C | 64.3 | 20.5 |  |
| Mif $CATT_{5-8}$ genotype |  |  |  |
| Allele frequency |  |  | <0.001 |
| 5 | 9.1 | 38.4 |  |
| 6 | 53.3 | 56.8 |  |
| 7 | 37.6 | 4.8 |  |
| Mif haplotype |  |  |  |
| Estimated frequency |  |  | <0.001 |
| G/5 | 5.9 | 32.6 |  |
| G/6 | 25.4 | 46.4 |  |
| G/7 | 4.2 | 0.7 |  |
| C/5 | 3.3 | 5.9 |  |
| C/6 | 28.6 | 10.4 |  |
| C/7 | 32.6 | 4.0 |  |

Allelic frequencies for both markers are significantly different between the prostate cancer and control groups (p<0.001). As reported previously there was high linkage disequilibrium between the two polymorphisms with the common haplotype distributions varying significantly between the prostate cancer and control groups6. The G/6 haplotype is the most common haplotype in the control group (46.4%), while the C/7 haplotype is the most common in the prostate cancer group (32.6%). These results point to a possible difference in the allelic distribution of Mif genotypes in the prostate cancer group compared to our control group. However, it is possible that in sampling bias was introduced since all of our samples are from a veteran population undergoing routine PSA screening. Since our sample size was small we compared the allelic and genotype frequency of our control and prostate cancer group with that of a previously reported Caucasian control group (the 7 non-Caucasian patients in our cohort were not included in this analysis since there appears to be racial variations in the population distribution of Mif alleles) (Zhong et al., Nucleic Acids Res 33: e121). There was no difference in the allelic frequency of −1 73 C (p=0.11) or the −794 CATT (p=0.09) polymorphisms between our control group and that reported previously. However, the allelic frequency of the prostate cancer group for both polymorphisms was different from that reported previously for Caucasian controls (p<0.0001).

Correlation of Mif −173 C and the −794 Mif $(CATT)_{5-8}$ polymorphisms with elevated serum MIF.

Figure 2:
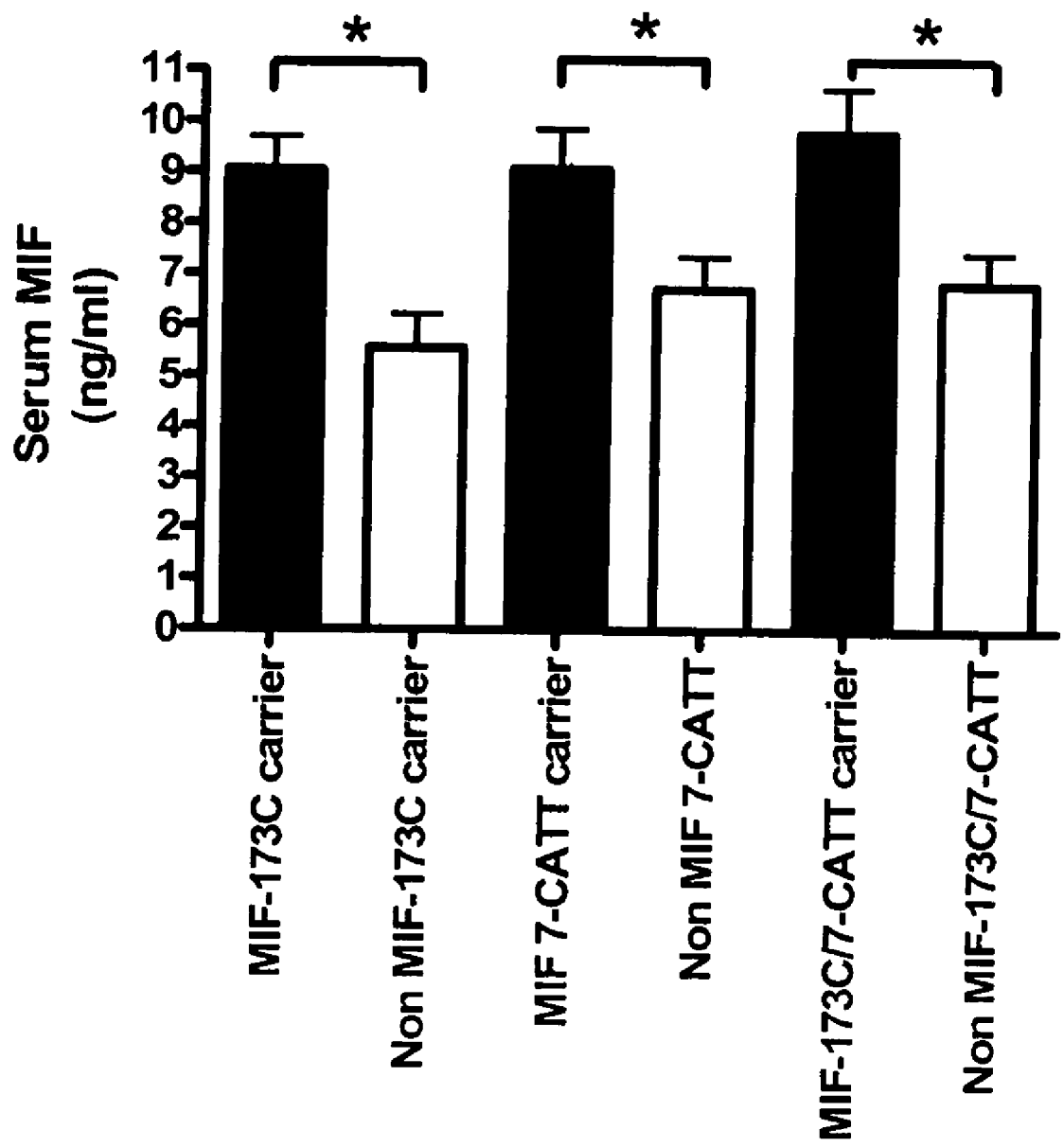
FIG. 2 is a graph showing the association of −173C and −749 $(CATT)_7$ with serum MIF amounts in prostate cancer patients.

We had previously established the association of elevated serum MIF with prostate cancer. In addition, it has been demonstrated that both of the functional Mif polymorphisms are associated with higher circulating MIF levels in patients with juvenile idiopathic arthritis (Donn et al., Arthritis Rheum 50:1604-1610, 2004) and rheumatoid arthritis (Radstake et al., Arthritis Rheum 52(10):3020-9, 2005). Therefore, we examined the association of Mif high expressing alleles (−173 C and/or −794 $(CATT)_7$) with serum MIF amounts in prostate cancer patients (n=74) (FIG. 2). Prostate cancer patients with either −173 C or −794 $(CATT)_7$ or both alleles in combination exhibited higher serum MIF amounts when compared to prostate cancer patients without the risk associated allele (p=0.013, 0.04, or 0.03 respectively). The combination of −173 C and −794 $(CATT)_7$ polymorphisms did not result in higher serum MIF amounts when compared with either risk allele alone.

Predictive Utility of Mif −173 C and the −794 Mif $(CATT)_{5-8}$ Polymorphisms for Prostate Cancer Comparison of the allele and estimated haplotype frequencies between prostate cancer and benign groups documented a difference (Table 1). Backward step-wise logistic regression was performed to assess whether these genotypes can be used to predict prostate cancer. Since our control group was significantly younger than the prostate cancer group and because increasing age is a prostate cancer risk factor all calculated odds ratios were age adjusted. Logistic regression demonstrated a statistically significant association between the G/C (OR 9.4, 95% CI 3.76-23.48, p<0.0001) and C/C (OR 20.9, 95% CI 6.78-64.38, p<0.0001) genotypes and the risk of prostate cancer (Table 2). The overall predictive utility of the generated model was 78.7% with 72.6% accuracy in predicting normal and 84.4% accuracy in predicting prostate cancer patients.

TABLE 2

Age adjusted odds ratio for the Mif-173 C polymorphism and prostate cancer risk.

| Mif-173 C genotype | No. Cases (%) | No. Controls (%) | Odds ratio (95% CI) | p Value |
|---|---|---|---|---|
| GG | 10 (13.0) | 49 (67.1) | 1.0 (reference) | — |
| GC | 35 (45.5) | 18 (24.7) | 9.40 (3.76-23.48) | <0.0001 |
| CC | 32 (41.5) | 6 (8.2) | 20.90 (6.78-64.38) | <0.0001 |
| GC or CC | 67 (87.0) | 24 (32.9) | 12.55 (5.36-29.37) | <0.0001* |

*Compared with GG genotype

Similar results were obtained with −794 CATT genotype in which logistic regression demonstrated a statistically significant association between the 5/7, 6/6, 6/7 and 7/7 and the risk of prostate cancer (Table 3). The overall predictive utility of the generated model was 80.7% with 82.2% accuracy in predicting normal and 79.2% accuracy in predicting prostate cancer patients.

utility of the generated model was 79.2% with 94.7% accuracy in predicting high grade tumors and 35% accuracy in predicting low grade tumors. There was no correlation between the presence of a single −794 (CATT)$_7$ allele and Gleason sum. In addition, combination of a single −173 C allele and −794 (CATT)$_7$ allele was no better at predicting high grade tumors than the −173 C allele alone (Table 5).

TABLE 3

Age adjusted odds ratio for the Mif (CATT)$_{5-8}$ polymorphism and prostate cancer risk.

| Mif(CATT)$_{5-8}$ genotype | No. Cases (%) | No. Controls (%) | Odds ratio (95% CI) | p Value |
|---|---|---|---|---|
| 5/5 | 1 (1.3) | 11 (15.0) | 1.0 (reference) | — |
| 5/6 | 5 (6.5) | 30 (41.1) | 1.85 (0.18-18.68) | 0.601 |
| 5/7 | 7 (9.1) | 4 (5.5) | 26.28 (2.15-320.85) | 0.010 |
| 6/6 | 23 (29.8) | 26 (35.6) | 9.73 (1.10-85.74) | 0.041 |
| 6/7 | 31 (40.3) | 1 (1.4) | 406.96 (21.57-7676.81) | <0.0001 |
| 7/7 | 10 (13.0) | 1 (1.4) | 93.67 (4.75-1846.97) | 0.003 |
| +7 | 48 (62.3) | 6 (8.2) | 21.89 (7.72-62.07) | <0.0001* |

7/8 or 8/8 genotype not detected

*Compared with no CATT$^7$ genotype

The predictive utility of the high expressing MIF genotypes combinations (C or (CATT)$_7$) were then assessed. The presence of both a −173C and −794 (CATT)$_7$ confers the highest risk of prostate cancer (OR 59.1, 95% CI 16.71-209.18.38, p<0.0001; Table 4). The overall predictive utility of the generated model was 81.3% with 80.8% accuracy in predicting normal and 81.8% accuracy in predicting prostate cancer patients.

TABLE 4

Age adjusted odds ratio for the high expressing Mif genotype combinations (−173 C or (CATT)$_7$) and prostate cancer risk.

| Mif Genotype | No. Cases (%) | No. Controls (%) | Odds ratio (95% CI) | p Value |
|---|---|---|---|---|
| No C/No 7 | 8 (10.4) | 48 (65.8) | 1.0 (reference) | — |
| +C or +7 | 23 (29.9) | 20 (27.3) | 6.05 (2.23-18.68) | <0.0001 |
| +C/+7 | 46 (59.7) | 5 (6.9) | 59.12 (16.71-209.18) | <0.0001 |

Correlation of Gleason Sum with Mif −173 C Functional Polymorphism in Prostate Cancer Patients The correlation between Mif polymorphisms and the histological degree of prostate cancer was determined in patients with low and high grade tumors as defined as Gleason sum less than 7 (low grade) and greater than or equal to 7 (high grade). Because of the small sample size the G/C and C/C genotypes were pooled and compared to the G/G genotype and the presence of a single −794 (CATT)$_7$ allele was compared to its absence. A strong association between high grade tumors and the presence of a −173 C allele was determined (OR 9.69, 95% CI 2.20-42.66, Table 5). The overall predictive These data suggest that the high expressing −173C MIF genotype closely correlates with prostate cancer aggressiveness.

TABLE 5

Age adjusted odds ratio for the high expressing Mif genotypes (C or (CATT)$_7$) and prostate tumor Gleason sum.

| Mif High Expressing Genotype | Gleason sum <7 No. (%) | Gleason sum ≧7 No. (%) | Odds ratio (95% CI) | p Value |
|---|---|---|---|---|
| +C | 13 (65) | 54 (94.7) | 9.69 (2.20-42.66) | .003 |
| +7 | 11 (55) | 37 (64.9) | 1.51 (0.54-4.26) | .433 |
| +C/+7 | 9 (45) | 37 (64.9) | 6.85 (1.38-34.14) | .019 |

Figure 3:
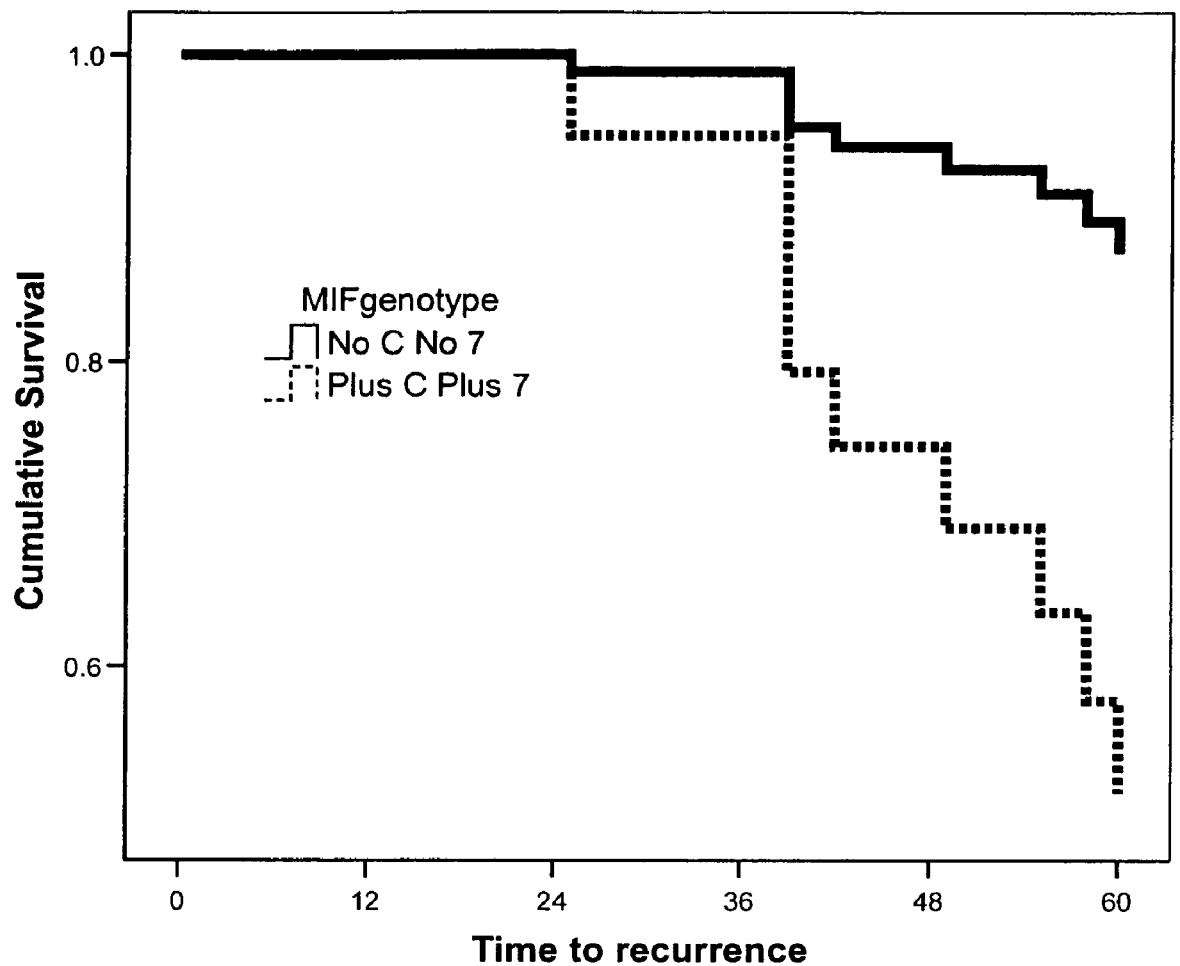
FIG. 3 is a graph showing the association of −173 and −749 $(CATT)_7$ with the recurrence of prostate cancer.

Predictive Utility for Prostate Cancer Recurrence Using Mif High Expressing Polymorphisms The relationship between Mif high expressing polymorphisms and prostate cancer recurrence (biochemical failure, defined as two PSA values of 0.4 ng/ml or greater and rising or initiation of adjuvant therapy five years post prostate cancer-diagnosis) was examined in 42 of the 77 prostate cancer patients for which repeated PSA determinations were available. We initially grouped these patients into 4 categories: no −173C and no (CATT)$_7$; plus −173C and no (CATT)$_7$; no −173C and plus (CATT)$_7$; and plus −173C and plus (CATT)$_7$. None of these 42 patients were in the no −173C and plus (CATT)$_7$ category. In addition, none of the no −173C and no (CATT)$_7$ patients recurred. Therefore, because of these factors and small sample size the genotypes were pooled such that the presence of a single −173C and −794 (CATT)$_7$ allele was compared to the absence of either −173C or −794 (CATT)$_7$ allele. Of the patients with the presence of a single −173C and −794 (CATT)$_7$ allele, 46.2% were diagnosed with recurrent disease within 5 years, whereas only 10.3% of the control group experienced recurrence (OR 4.80, 95% CI 1.20-19.25, p=0.027) (FIG. 3).

Although certain presently preferred embodiments of the invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. A method for determining the risk of, detecting, diagnosing, or prognosticating prostate cancer in an individual, comprising the steps of testing the individual for the presence of a −173 C mutation or a CATT repeat in the promoter of the macrophage migration inhibitory factor (MIF) gene, wherein the CATT repeat is 7 or higher repeats locating at position −749, and wherein the testing step comprises
   a) collecting a nucleic acid sample from the individual;
   b) amplifying the nucleic acid sample; and
   c) sequencing the promoter of the MIF gene.

2. The method of claim 1, wherein the promoter of the MIF gene has the nucleotide sequence of nucleotides 1 to 1263 of SEQ ID NO: 1.

3. The method of claim 1, wherein the nucleic acid is DNA.

4. The method of claim 1, further comprising the step of determining the amount of prostate specific antigen in the individual.

5. The method of claim 1, wherein the CATT repeat is $(CATT)_7$.

* * * * *